United States Patent [19]
Cobian et al.

[11] Patent Number: 5,796,044
[45] Date of Patent: Aug. 18, 1998

[54] COILED WIRE CONDUCTOR INSULATION FOR BIOMEDICAL LEAD

[75] Inventors: Kenneth E. Cobian, St. Anthony; Michael J. Ebert, Fridley; Peter B. McIntyre, Moundsview; David W. Mayer, Bloomington, all of Minn.

[73] Assignee: Medtronic, Inc., Minneapolis, Minn.

[21] Appl. No.: 797,435

[22] Filed: Feb. 10, 1997

[51] Int. Cl.$^6$ .................................................. A61N 1/05
[52] U.S. Cl. .............................. 174/103; 174/113 AS; 607/119; 607/122
[58] Field of Search ........................ 174/103, 113 AS, 174/117 AS, 152 GM; 607/116, 119, 122, 123, 125, 126, 127, 128

[56] References Cited

U.S. PATENT DOCUMENTS

| | | | |
|---|---|---|---|
| 3,333,045 | 7/1967 | Fisher et al. | 174/20 |
| 3,348,548 | 10/1967 | Chardack | 607/122 |
| 3,472,234 | 10/1969 | Tachick | 607/131 |
| 3,788,329 | 1/1974 | Friedman | 607/122 |
| 4,000,745 | 1/1977 | Goldberg | 607/127 |
| 4,640,983 | 2/1987 | Comte | 174/119 R |
| 4,662,382 | 5/1987 | Sluetz et al. | 607/126 |
| 4,860,446 | 8/1989 | Lessar et al. | 29/858 |
| 4,922,607 | 5/1990 | Doan et al. | 29/879 |
| 4,947,866 | 8/1990 | Lessar et al. | 607/116 |
| 5,007,435 | 4/1991 | Doan et al. | 607/119 |
| 5,132,488 | 7/1992 | Tessier et al. | 174/34 |
| 5,483,022 | 1/1996 | Mar | 174/128.1 |

FOREIGN PATENT DOCUMENTS

| 1146228 | 5/1983 | Canada. |
|---|---|---|

OTHER PUBLICATIONS

Adler, S. et al, "Thin Bipolar Leads: A Solution to Problems with Coaxial Bipolar Designs", *PACE*, vol.15, Nov. Part II 1992.

*Primary Examiner*—Kristine L. Kincaid
*Assistant Examiner*—Marc D. Machtinger
*Attorney, Agent, or Firm*—Reed A. Duthler; Harold R. Patton

[57] ABSTRACT

A biomedical lead conductor body formed of a coiled wire conductor that is sheathed loosely within a coiled insulative sheath of biocompatible and biostable material allowing a gap or space to be present between the exterior surface of the coiled wire conductor and the adjacent interior surface of the insulative sheath. The coiled insulative sheath is loosely fitted around the coiled wire conductor in order to compensate for defects in the coiled insulative sheath by spreading any corrosion of the wire that may take place because of the defect away from the site of a defect and along the surface of the coiled wire conductor. The lead body is incorporated into unipolar, bipolar or multi-polar biomedical leads having single filar coil windings, or multi-filar coil windings that may be redundantly electrically connected. The coiled wire conductors and coiled insulative sheaths may be parallel-wound and/or coaxially wound within the outer lead body insulative sheath. The individual coiled wire conductors may be formed of single filar wire or multi-filar wire cable and formed of single composition or composite conductive metals. The proximal and distal wire ends of the coiled wire conductors that are electrically connected in common are connected to lead connector elements and operative elements, respectively.

31 Claims, 8 Drawing Sheets

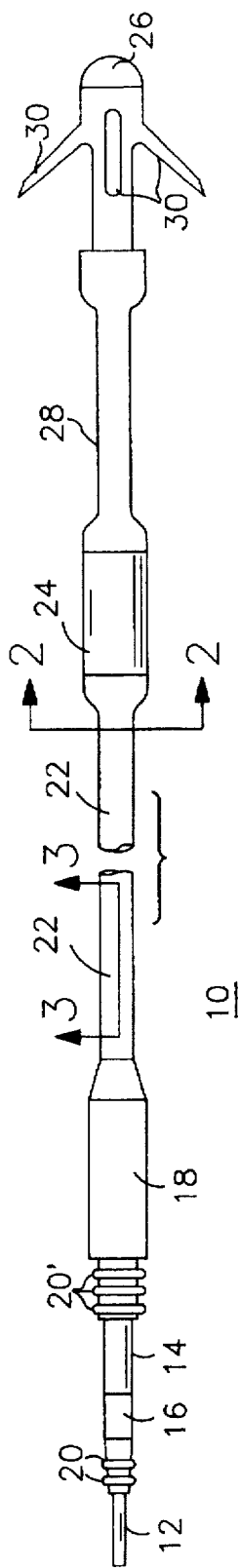
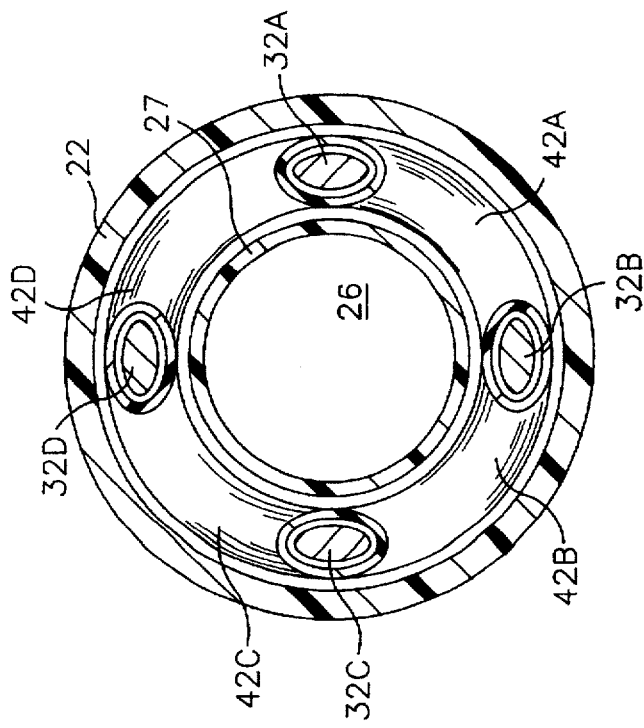
FIG. 1
FIG. 2

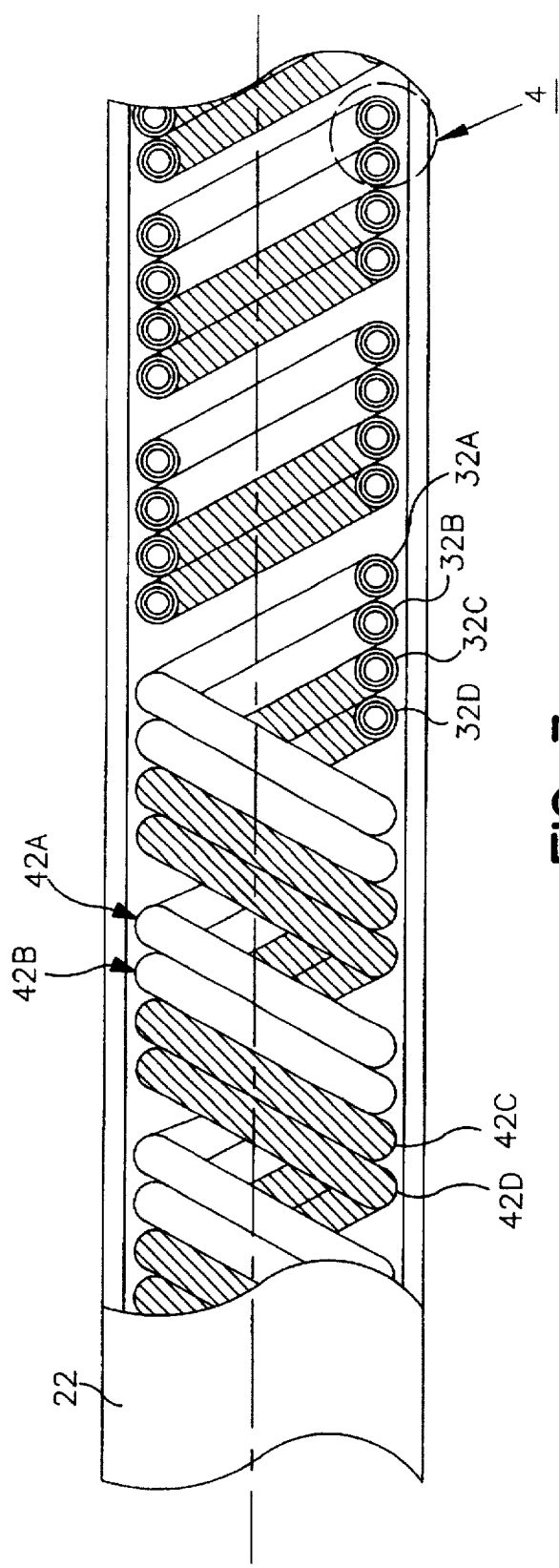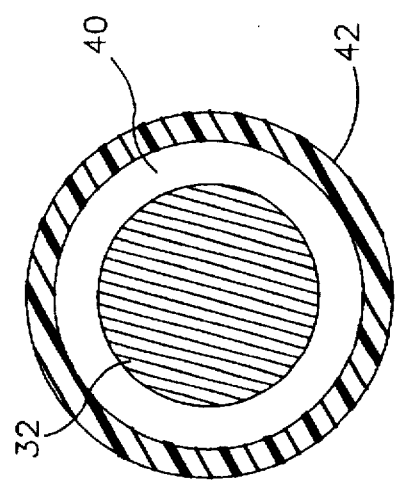

COILED WIRE CONDUCTOR INSULATION FOR BIOMEDICAL LEAD

CROSS-REFERENCE TO RELATED APPLICATIONS

Reference is hereby made to commonly assigned, co-pending U.S. patent application Ser. No. 08/711,829 filed Sep. 10, 1996, in the names of Timothy G. Laske et al. for CONDUCTOR CABLE FOR BIOMEDICAL LEAD.

FIELD OF THE INVENTION

The present invention relates generally to the field of body implantable medical leads and lead conductors, particularly to parallel-wound and/or coaxially wound, coiled wire conductors in a lead body, each coiled wire conductor of a given polarity separately insulated from the other coiled wire conductor(s) of other polarities by a coiled insulative sheath loosely receiving the coiled wire conductor(s).

BACKGROUND OF THE INVENTION

As noted in U.S. Pat. No. 5,483,022, the human body is a hostile environment to implanted medical devices and materials, particularly to chronically implanted medical leads, including cardiac leads which extend into a heart chamber or cardiac vessel or contact the exterior of the heart. Implantable cardiac leads are typically coupled at their proximal ends with implanted pacemaker and pacemaker/cardioverter/defibrillator pulse generators and cardiac monitors and extend to a distal end located through a transvenous introduction approach within a heart chamber or attached to the exterior of the heart. The heart beats approximately 100,000 times per day or over 30 million times a year, and each beat stresses at least the distal end portion of the lead. Over the years of implantation, the lead conductors and insulation are subjected to cumulative mechanical stresses, as well as material reactions as described below, that can result in degradation of the insulation or fractures of the lead conductors with untoward effects on device performance and patient well being.

The lead conductor typically employed in such cardiac leads is a single wire coil or a multi-filar wire coil used alone, in a unipolar lead configuration for coupling a single distal electrode with a single proximal connector element, or used in an electrically isolated polarity pair, in a bipolar lead configuration for coupling two distal electrodes with two proximal connector elements. Most early designs of chronically implanted cardiac leads, as well as other implantable leads, used tubular insulative sheaths having lumens for separately receiving and electrically insulating each coiled wire conductor from the body environment and from any other coiled wire conductor incorporated into the lead.

Early implantable, transvenous and epicardial, bipolar cardiac pacing leads of the type disclosed in U.S. Pat. No. 3,348,548 placed the separate coiled wire conductors in a side by side configuration and incorporated a lumen for receiving a stiffening stylet inside the lumen of at least one of the conductor coils. This design was replaced by a coaxial configuration of the type shown in U.S. Pat. No. 3,788,329 wherein the separate coiled wire conductors are wound in differing diameters separated from one another by tubular insulative sheaths and extend coaxially about a central lumen for receiving the stiffening stylet. Most current transvenous cardiac leads employ multi-filar, parallel-wound, coiled wire conductors electrically connected in common in an electrically redundant fashion as a single polarity lead conductor in each of the unipolar, bipolar and multi-polar lead configurations. Such redundant coiled wire conductors of bipolar and multi-polar lead bodies are coaxially arranged about the stiffening stylet receiving lumen and insulated from one another by coaxially arranged insulative sheaths separating each coiled wire conductor from the adjacent coiled wire conductor(s).

For many years, the exterior insulative sheaths and the interior separating sheaths of bipolar and multi-polar leads have been formed of bio-compatible silicone rubber. More recently developed, chronically implanted, medical leads have employed commercially available polyether urethanes or polyurethanes due to their superior mechanical properties. These include Pellethane 80A and Pellethane 55D polyurethanes manufactured by Dow Chemical Company which are less thrombogenic than silicone rubber and higher in tensile strength. Therefore, sheaths formed of these materials may be made thinner than sheaths made of silicone rubber, thereby markedly reducing the lead body outer diameter. In addition, lead bodies formed of these polyurethanes slide easily against one another when moistened with blood. The combination of reduced lead body outer diameter and the slippery surface facilitate the use of two leads in a single vein, which was difficult with the older silicone rubber lead bodies.

Unfortunately, recent experience has also suggested that metal ion migration of cobalt, chromium and molybdenum, commonly used in lead conductors, may accelerate oxidative degradation of these low durometer polyurethanes used in pacing lead insulative sheaths. Cardiac lead conductor wires have been formed of a single conductive metal, e.g., stainless steel or a noble metal, but at this time are typically formed of an alloy material, e.g. MP 35N alloy or Elgiloy® alloy, or of a composite conductive material that all include cobalt, molybdenum and chromium as significant constituents. In one response to this problem set forth in commonly assigned U.S. Pat. No. 5,040,544, it has been suggested that the exterior surface of the wire be coated with a barrier coating of a noble metal that does not itself cause the reaction to occur and inhibits migration of these metal ions.

The typically used composite conductive material wires are formed with a silver core, to provide increased conductivity, clad with MP 35N alloy or surgical grade stainless steel or the like to encase the silver core, in a drawn brazed stranded (DBS) fabrication process or a drawn filled tube (DFT) fabrication process well known in the art and described, for example, in U.S. Pat. Nos. 3,333,045 and 4,640,983 and in the above-referenced '022 patent. Pacing lead conductors are expected to conduct currents of less than 1 mA at voltages less than 10 volts and have a lead resistance of between 40–200 ohms. The principal reasons for reducing pacing lead impedance have been for sense amplifier and electrode impedance matching and to decrease pacing pulse current consumption to prolong battery life.

However, the lead conductors employed to deliver cardioversion/defibrillation shocks are subjected to high currents of about 35 amps at 300–800 volts. It is desirable that the cardioversion/defibrillation lead resistance be far lower, on the order of less than 10 ohms. Consequently, the cardioversion/defibrillation lead conductor configurations have a greater cross-section wire gauge and use noble metals to clad the conductor wire(s) or use the DBS type composite wire conductor to a greater extent. The highly conductive noble metals are both expensive and certain of them are relatively weak and subject to fracture under the applied cardiac stresses, and therefore cannot be used as the principal lead conductor material. In addition, the non-noble, highly conductive metals or metal alloys, including silver, aluminum and copper, cannot be exposed to body fluids since they corrode or migrate when so exposed, further weakening and increasing the resistance of the wire. Despite the best efforts to prevent body fluid intrusion into biomedical leads, the long term exposure in chronic implantation makes it likely that fluid intrusion will eventually occur.

In the implantation of a cardiac device of the types listed above, and in the replacement of previously implanted cardiac leads, two or more transvenous cardiac leads are typically introduced through the venous system into the right chambers of the heart. As noted above, it has long been desired to minimize the diameter of the transvenous cardiac lead body to facilitate the introduction of several cardiac leads by the same transvenous approach. Moreover, a number of multi-polar, endocardial cardiac leads have been designed to accommodate more than two electrodes or to make electrical connection with other components, e.g., blood pressure sensors, temperature sensors, pH sensors, or the like, in the distal portion of the lead. The increased number of separate polarity coiled wire conductors is difficult to accommodate in the conventional coaxial coiled wire conductor winding arrangement emptying tubular insulative sheaths to separate the coil wire conductors of differing diameters having a desired overall lead body outer diameter.

This need for increased numbers of lead conductors in the lead body has led to the development of separately insulated, coiled wire conductors that are parallel-wound with a common diameter and are separately coupled between a proximal connector element and to a distal electrode or terminal. The coaxial construction technique may also be combined with the parallel-winding technique to multiply the total number of separate coiled wire conductors accommodated within a specified endocardial lead body outer diameter.

Another reason for developing separately insulated coiled wire conductors is to provide a biostable insulator barrier between the surface of the coiled wire conductor and any adjacent sheathes formed of the aforementioned low durometer polyurethanes susceptible to reaction with the aforementioned metals. Effective Insulation of the coiled wire conductor surface with a PTFE or ETFE coating would allow the use of these polyurethane materials in lead body outer sheaths and in inner separating sheaths for coaxially wound coiled wire conductors.

Long before these problems and needs were recognized, it was proposed that coiled lead conductor wires be separately insulated with an insulative coating adhering tightly to the wire surface. Early versions of separately insulated, coiled wire conductors in side-by-side and parallel-wound configurations, particularly for epicardial lead bodies, are shown, for example, in U.S. Pat. Nos. 3,472,234 and 4,000,745, respectively. In these cases, it is suggested that the coiled wire conductors be coated or extruded with Teflon® polytetrafluoroethylene (PTFE) or silicone rubber or other insulating materials known at the time.

The above-referenced '045 patent suggests a different approach wherein side-by-side DBS coiled wire conductors are encased within straight silicone rubber tubes that are filled with a silicone rubber fluid and sealed at each end to hopefully prevent body fluid intrusion. The straight silicone rubber tubes are then enclosed within the lumen of an outer silicone rubber sheath. These approaches of the '045, '234 and '745 patents are intended for epicardial pacing leads where lead body outer diameter is not as great a consideration as it is in endocardial pacing leads.

More recent endocardial lead bodies of the type employing separately insulated, parallel-wound coiled wire conductors are disclosed, for example, in U.S. Pat. Nos. 4,662,382, 4,922,607, and 5,007,435, in Canadian Patent No. 1,146,228, for a Multipolar Pacing Conductor, issued May 10, 1983 to Upton, as well as in the article by S. Adler et al., entitled "Thin Bipolar Leads: A Solution to Problems with Coaxial Lead Designs" published in *PACE* (November, Part II 1992, 15:1986–90). In these more recent endocardial leads, the insulation of each conductor wire coil is effected by application of a coating layer or the extrusion of a polymer against the wire surface to form a tight, intimate bond with it. Typically, these references suggest that either a polyurethane or an ethylene tetrafluoroethylene (ETFE) or a PTFE-type coating layer be created by deposition techniques or by extrusion about the wire to form a tight bond with the wire surface. Silicone rubber coatings have not been proposed because it is generally recognized that the required coating thickness to provide effective insulation would be too great to operate effectively with the small diameter conductor wires and lead body diameters proposed for use in leads of this type. As mentioned above, it is hoped that such coatings can be employed to prevent metal ion migration and allow use of low durometer polyurethane outer sleeve bodies with a greater degree of confidence.

Recently, we have found that defects in the polymer coatings of such coiled wire conductors arise during manufacture or as a result of implantation trauma or as a result of post-implantation stress and motion. During implantation, the lead body insulative sheath and the conductor wire coating layer may be inadvertently cut. As a result of heart motion, wear and abrasion or stress induced creep and cold flow of the coating layer may occur, causing it to thin and eventually expose the wire surface. In addition, the coating and extrusion processes can leave microscopic flaws and/or pin hole defects that are not readily detectable. The flaws or pin hole defects can operate as sites for the introduction of body fluids and cause localized corrosion of the underlying, adjacent wire, which can be accelerated in the presence of applied electrical energy, e.g. pacing pulses.

The localized corrosion of the conductor wire is concentrated at the defect site, and with small diameter conductor wires, the corrosion can eventually cause a fracture of the wire, particularly if it is being flexed or otherwise stressed at the site. The chemical reaction may itself increase the rate and extent of deterioration of the coating layer, leading to a greater exposure of the conductor wire surface and possibly electrical shorting of adjacent coiled wire conductors of different polarities.

Thus, despite these improvements, a need remains for a medical lead employing a miniaturized conductor cable configuration with improved survival in chronic implantation over the long term and providing suitable current carrying capacity for conducting pacing pulse or cardioversion/defibrillation shock energy.

SUMMARY OF THE INVENTION

Accordingly, it is an object of the present invention to provide an improved insulation technique for coiled wire medical lead conductors that does not cause localized corrosion to occur in the area of a localized defect in the insulation.

It is a further object of the present invention to provide such an improved insulation technique for parallel-wound coiled wire medical lead conductors for insulating adjacent coiled wire conductor turns from one another.

It is yet a further object of the present invention to provide such an insulation technique that operates to ameliorate the effects of minute defects in the insulation.

These and other objects of the present invention are realized in a medical lead body formed of a coiled wire conductor that is sheathed loosely within a separate coiled insulative sheath allowing a gap or space to be present between the exterior surface of the coiled wire conductor and the adjacent interior surface of the insulative sheath. The insulative sheath is loosely fitted around the coiled wire conductor to avoid concentrating corrosion effects at the site of a defect, allowing any corrosion that may occur as a result of the defect to be spread over a larger wire surface. The coiled insulative sheath is preferably included within the lumen of a non-coiled outer insulative sheath.

The biomedical lead body preferably comprises at least a first coiled wire conductor having a predetermined wire diameter and wound into a first coil extending between proximal and distal coiled wire conductor ends, and a first insulative sheath formed in a coil and having an insulative sheath lumen having a diameter exceeding the predetermined wire diameter of the first coiled wire conductor for loosely receiving the first coiled wire conductor therein for electrically insulating the coil turns of the first coiled wire conductor along its length.

Preferably, the lead body is of a bipolar or multi-polar configuration and includes a second coiled wire conductor formed of a second electrical wire having a predetermined wire diameter and wound into a second coil extending between proximal and distal second wire ends. The first and second coiled wire conductors are preferably parallel-wound with one another in an intertwined relation about a substantially common winding diameter or coaxially wound with differing winding diameters. The coiled insulative sheath loosely receives the first coiled wire conductor therein for electrically insulating the coil turns of the first coiled wire conductor from the adjacent coil turns of the second coiled wire conductor and for avoiding concentrated damage to the first coiled wire conductor within and adjacent to a defect in the first coiled insulative sheath.

Preferably, the biomedical lead conductor body further comprises a second insulative sheath formed in a coil and having a second insulative sheath lumen having a diameter exceeding the predetermined wire diameter of the second coiled wire conductor for loosely receiving the second coiled wire conductor therein for electrically insulating the adjacent coil turns of the first coiled wire conductor and the second coiled wire conductor and for avoiding concentrated damage to the second coiled wire conductor within and adjacent to a defect in the second coiled insulative sheath enclosing it.

In a similar fashion, each or selected ones or groups of coiled wire conductors in unipolar, bipolar and multi-polar leads may be individually insulated within coiled insulative sheaths. Moreover, in parallel-wound conductor wire configurations wherein a plurality of coiled wire conductors are electrically connected in common in a redundant fashion, the coiled insulative sheath may be configured to receive two or more redundantly connected coiled wire conductors within its lumens.

The coiled wire conductors may be coupled to proximal connector elements and to operative elements, e. g. electrodes or sensors, formed in the distal region of the lead body to form an implantable medical lead. The coiled insulative sheaths may be extruded about the wire conductor in a manner that results in the space or gap between the inner surface of the coiled insulative sheath lumen and the wire The coiled insulative sheaths may be formed of a wide variety of bio-compatible and biostable materials including certain polyurethanes and PTFE-type materials as specified herein.

Advantageously, the coiled wire insulative sheaths loosely receiving the coiled wire conductors decrease the probability that defects in the coiled wire insulative sheath will result in mechanical fracture or deterioration of the lead conductor or unacceptable changes in electrical resistance. Therefore, the conductor wire diameter may be reduced and the advantages of miniaturized parallel-wound and/or coaxially wound, multi-polar lead bodies may be realized.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 1 is a schematic illustration of an exemplary medical lead, specifically an endocardial cardiac lead in which the present invention may be implemented;

FIG. 2 is an idealized end cross-section view of the catheter body taken along lines 2—2 of FIG. 1 showing the lead body construction in accordance with a first embodiment of the invention;

FIG. 3 is an idealized cross-section view of the catheter body taken along lines 3—3 of FIG. 1 showing the parallel winding of coiled wire conductors, employing a single filar conductor wire;

FIG. 4 is an end cross-section view taken at section 4 in FIG. 3 of a single coiled wire conductor received within the lumen of a coiled insulative sheath;

Figure 5:
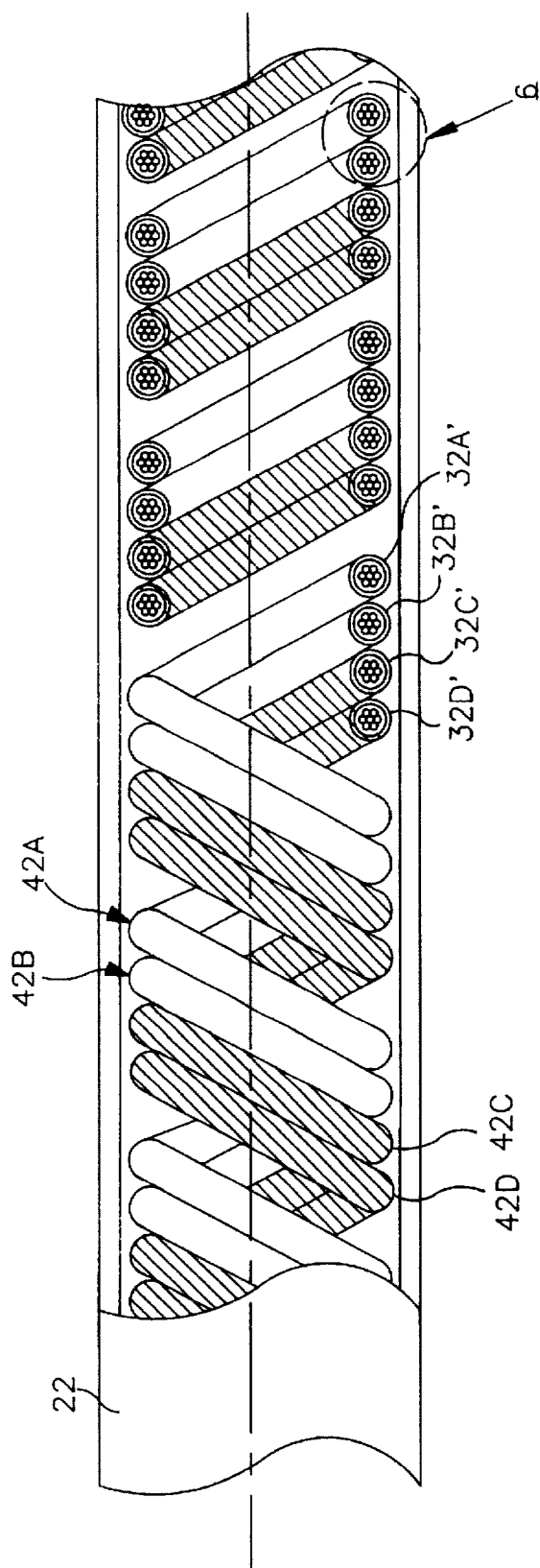
FIG. 5 is an idealized cross-section view of the catheter body also taken along lines 3—3 of FIG. 1 showing the parallel winding of coiled wire conductors, employing a 7×7 filar cable conductor wire.

The drawing figures are not necessarily to scale.

DETAILED DESCRIPTION OF THE PREFERRED EMBODIMENTS

The implantable lead conductor cable of the present invention is preferably embodied in the construction of an implantable, endocardial pacing or cardioversion/defibrillation lead for conducting cardioversion/defibrillation shocks from an implantable cardioverter/defibrillator or pacemaker/cardioverter/defibrillator to a distal electrode and to the patient's heart in direct or indirect contact therewith. However, the coiled wire conductor insulation technique of the present invention, in all of the embodiments thereof, may also advantageously be used in any other medical lead intended for chronic implantation employing one or more electrodes or other operative elements.

FIG. 1 is a plan view of an exemplary endocardial cardiac pacing or cardioversion/defibrillation lead according to the present invention wherein at least two parallel-wound coiled wire conductors are insulated from one another by a coiled, loose insulative jacket or sheath that allows a slight space between the conductor wire coils and the surrounding sheath coils. The exterior of the exemplary cardiac lead 10 includes a connector assembly at its proximal end, including a conductive pin 12, a conductive ring element 14, and two insulative segments 16 and 18. Insulative segments 16 and 18 are each provided with a plurality of sealing rings 20 for sealing the proximally disposed connector pin 12 and ring element 14 within an elongated socket in a connector block of the implantable medical device the cardiac lead 10 is connected with. Extending from the connector assembly is an elongated lead body, including an outer insulative sheath 22, which is preferably fabricated of polyurethane, e.g., Pellethane 80A and Pellethane 55D, both products of Dow Chemical Co., and coiled wire conductors disposed therein in accordance with the present invention.

A proximal ring electrode 24 and a distal tip electrode 26, separated by a distal insulative sleeve 28, are disposed in the distal end segment of the lead body. The proximal ring electrode 24 and the distal tip electrode 26 are electrically coupled to the proximal ring connector element 14 and the connector pin 12, respectively, by at least one coiled wire conductor in a manner shown, for example, in the above-referenced '607 and '453 patents, incorporated herein by reference in their entireties. In accordance with the present invention, each parallel-wound, coiled wire conductor (or redundant group of conductors) is threaded within a separate loosely fitting, coiled sheath so that the coiled wire surface is slightly spaced from the surrounding coiled insulation sheath as illustrated in the remaining figures. The assembly of the parallel-wound coiled wire conductors insulated within the coiled insulation sheaths is itself encased within outer insulative sheath 22. For example, each coiled wire conductor may itself be a single wire or a multi-filar wire, and in either case, both coiled wire conductors may be wound in a single diameter, parallel winding technique as described in the above-referenced '544 patent and in the bipolar embodiments of the above-incorporated '607 and '435 patents. The wire conductor may be of any of the compositions and manufactures described above, and may be coated with a barrier coating as described in the above-referenced '544 patent, incorporated by reference.

Cardiac leads 10 intended to be implanted in the right atrium or the right ventricle typically employ active or passive, distal end fixation mechanisms, which may or may not constitute a distal electrode, to maintain contact of the distal electrode 26 with endocardial or myocardial tissue to ensure adequate stimulation or sensing. For example, such fixation mechanisms include active, retractable/extendable helical coils (not shown) adapted to be extended and screwed into the myocardium at the desired site and passive, soft pliant tines 30 (of the type described in commonly assigned U.S. Pat. No. 3,901,502) typically formed of silicone rubber or polyurethane which engage in interstices in the trabecular structure to urge a distal tip electrode into contact with the endocardium. The atrial pacing lead may be formed with a J-shaped bend that allows the atrial electrode to be positioned in the atrial appendage and fixed there through use of the fixation mechanism.

Such pace/sense distal tip electrodes and fixation mechanisms are also currently used in conjunction with large surface area cardioversion/defibrillation electrodes extending proximally along the length of the lead sheath for either right atrial or ventricular placement. Separate electrical conductors and connectors are employed to connect the atrial cardioversion/defibrillation electrodes with an implantable pulse generator connector terminal for applying cardioversion/defibrillation shock energy to the respective heart chamber. In this variation, electrode 24 may be considered to represent an elongated cardioversion/defibrillation electrode of any of the well known types.

FIGS. 2 and 3 show end and side cross-section views through the lead 10 of FIG. 1, intermediate the connector assembly and the ring electrode 24. In these views, a quadrifilar coil within outer insulative sheath 22 is visible. This coil consists of four individual coiled wire conductors 32A, 32B, 32C and 32D which are all parallel-wound in an interlaced manner to have a common inner and outer coil diameter. The four individual coiled wire conductors 32A, 32B, 32C, 32D are loosely received within lumens of, and electrically insulated from one another by, insulative sheaths 42A, 42B, 42C and 42D, respectively. Insulative sheaths 42A, 42B, 42C and 42D are also formed to have the same coil axis diameter and pitch as the enclosed coiled wire conductors 32.A, 32B, 32C, and 32D. The insulated, multifilar coil is provided with an internal lumen 26, which allows for the passage of a stylet. An inner insulative liner or sheath 27 within lumen 26 may be provided to protect conductors 32A, 32B, 32C and 32D from nicks that might otherwise occur due to passage of the stylet. The inner sheath 27 is not shown in FIG. 3 for convenience of illustration.

FIG. 4 shows an end cross-section of one of the individual coiled wire conductors 32 among coiled wire conductors 32A, 32B, 32C, 32D, forming the multi-filar coil of FIG. 2 and its surrounding loose insulative sheath 42. In the case of each of the coiled wire conductors 32A, 32B, 32C, 32D, the loosely coiled, insulative sheath 42A, 42B, 42C, 42D is separated from the surface of the coiled wire conductor 32 by a gap or space 40.

In this example, the coiled wire conductors 32A, 32B, 32C, 32D may be on the order of about 0.001–0.0010 inches in diameter. The space 38 may be on the order of about 0.001 inches, and the loose, coiled insulative sheaths 42A, 42B, 42C, 42D may be about 0.0005–0.0050 inches (0.003 inches nominal) thick. The insulated coiled wire conductors may be wound into two coaxial coils having an inner coil diameter of about 0.005 inches and an outer coil diameter of about 0.012–0.062 inches. When the outer insulative sheath 22 is fitted over it, the lead body diameter may be on the order of about 0.026–0.082 inches.

Figure 6:
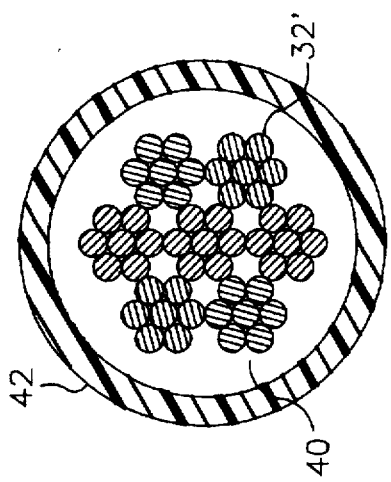
FIG. 6 is an end cross-section view taken at section 6 in FIG. 5 of a single coiled wire conductor received within the lumen of a coiled insulative sheath.

FIG. 5 shows a further side cross-section view through the lead 10 of FIG. 1, intermediate the connector assembly and the ring electrode 24 wherein the coiled wire conductors 32' are formed of 7×7 cables of wire filars wound together in the manner described in the above-referenced '045 and '022 patents. FIG. 6 shows a cross-section of one of the individual coiled wire conductors 32' among coiled wire conductors 32A', 32B', 32C', 32D', forming the multi-filar cable and its surrounding loose insulative sheath 42. In the case of each of the coiled wire conductors 32A', 32B', 32C', 32D', the loosely coiled, insulative sheath 42A, 42B, 42C, 42D is separated from their surfaces by a gap or space 40. In these views, the 7×7 cable filars may be formed of a single metal or metal alloy or formed using the above-referenced DBS and DFT techniques. Again, the inner sheath 27 of FIG. 2 is not shown in FIG. 5 for convenience of illustration.

The coiled wire conductors 32A, 32B, 32C, 32D shown in FIGS. 3 and 5 may be divided into pairs that are electrically and mechanically connected between the electrodes 24 and 26 and the connector ring element 14 and connector pin 12 to establish a redundant electrical connection in each case. The shading of the pair comprising the coiled wire conductors 32C, 32D and coiled insulative sheaths 42C, 42D indicates that they are electrically connected together to form a bipolar lead. It will be understood that the number of connector elements and electrodes may be increased up to four each just using a single separately insulated coiled wire conductor 32A–32D. Of course, additional coiled wire conductors can be intertwined into the depicted coil to accommodate additional electrodes or make the electrical connections redundant.

Moreover, if additional current carrying capacity is required, e.g., when ring electrode 24 is an elongated cardioversion/defibrillation electrode, all of the coiled wire conductors 32A–32D or 32A'–32D' may be electrically connected in common. The distal tip electrode 26 and the proximal connector pin 12 may be electrically connected by a further single or multi-filar coiled wire conductor coaxially extended down the inner lumen 26. However, the overall diameters of depicted structure would have to be enlarged in order to retain a usable diameter inner lumen for receiving a stiffening stylet.

In this regard, the present invention may also be implemented in a unipolar lead having only a single distal operative element coupled through one or more coiled wire conductors to a single proximal connector element, e.g. connector pin 12. For example, in FIGS. 1–6, all four of the coiled wire conductors 32A–32D or 32A'–32D' may be electrically connected in common so that the conductors have only one polarity. This particular configuration may be employed as a unipolar pacing lead employing distal tip electrode 26 as the operative element or as a unipolar cardioversion/defibrillation lead employing an elongated ring electrode 24 as the operative element.

Figure 7:
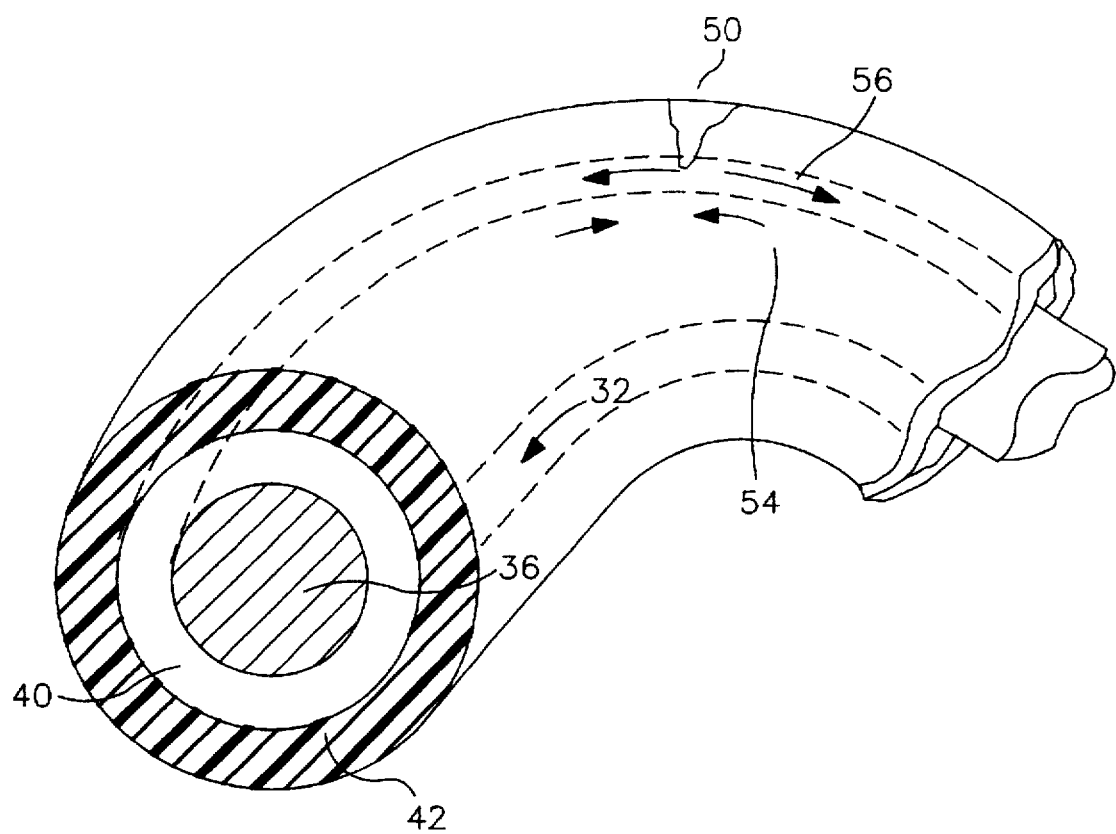
FIG. 7 is a partial cross-section view of a coil section of the insulative sheath and the coiled wire conductor loosely received within the coiled insulative sheath lumen and the effects of a localized defect in the insulative sheath.

Turning to FIG. 7, it depicts a coil section of the insulative sheath 42 and an exemplary coiled wire conductor 32 loosely received within the insulative sheath lumen and the effects of a localized defect 50 in the insulative sheath 42. In this case, body fluids that may be in the lumen of outer insulative sheath 22 migrate in fluid pathways 52 through the space 40. To the extent that corrosion or other material reactions take place, they do so spread out along the surface of the coiled wire conductor 32 in corrosion pathways 54. The corrosion or reaction is less likely to penetrate into the wire and weaken it to the point that it fractures.

As described above, one of the reasons why it has been considered desirable to coat coiled wire conductors with individual insulative coatings or noble metal coatings was to reduce the contact reaction between the conductor wire and certain low durometer polyurethane materials preferred for use as straight insulative sheaths, e.g. the outer insulative sheath 22. The insulative sheath 42 largely accomplishes the desired isolation, despite the localized defect 50, because it still isolates the bulk of the conductor wire from actual contact with the outer insulative sheath 22 and minimizes metal ion migration or other reactions. The overall survivability of the lead is enhanced because the conductor wire integrity is more likely to be preserved than in the case where the conductor wire is coated with a tightly adhering insulative coating or a noble metal coating. Thus, all of the perceived benefits of such coatings are obtained without the deleterious effects caused by localized defects in them. The techniques of forming the endocardial cardiac lead body described above may be employed in any implantable lead body for making a connection between one or more connector elements at the proximal end thereof and one or more respective operative elements formed distal to or within the distal outer sheath end region. The operative elements as described above with reference to FIG. 1 constitute pace/sense electrodes 26 and 24. It will be understood that the operative elements may comprise one or more cardioversion/defibrillation electrodes or sensors. In the field of cardiac pacing, a number of sensors have been proposed for incorporation into the endocardial lead body in substitution for or conjunction with the ring electrode 24, e.g., blood oxygen, pressure, temperature and pH sensors as well as blood gas sensors. In certain of these cases, the sensor itself may require more than one electrical lead conductor. The present invention may also be incorporated into lead bodies having more than two operative elements as depicted in FIGS. 1–6.

Figure 8:
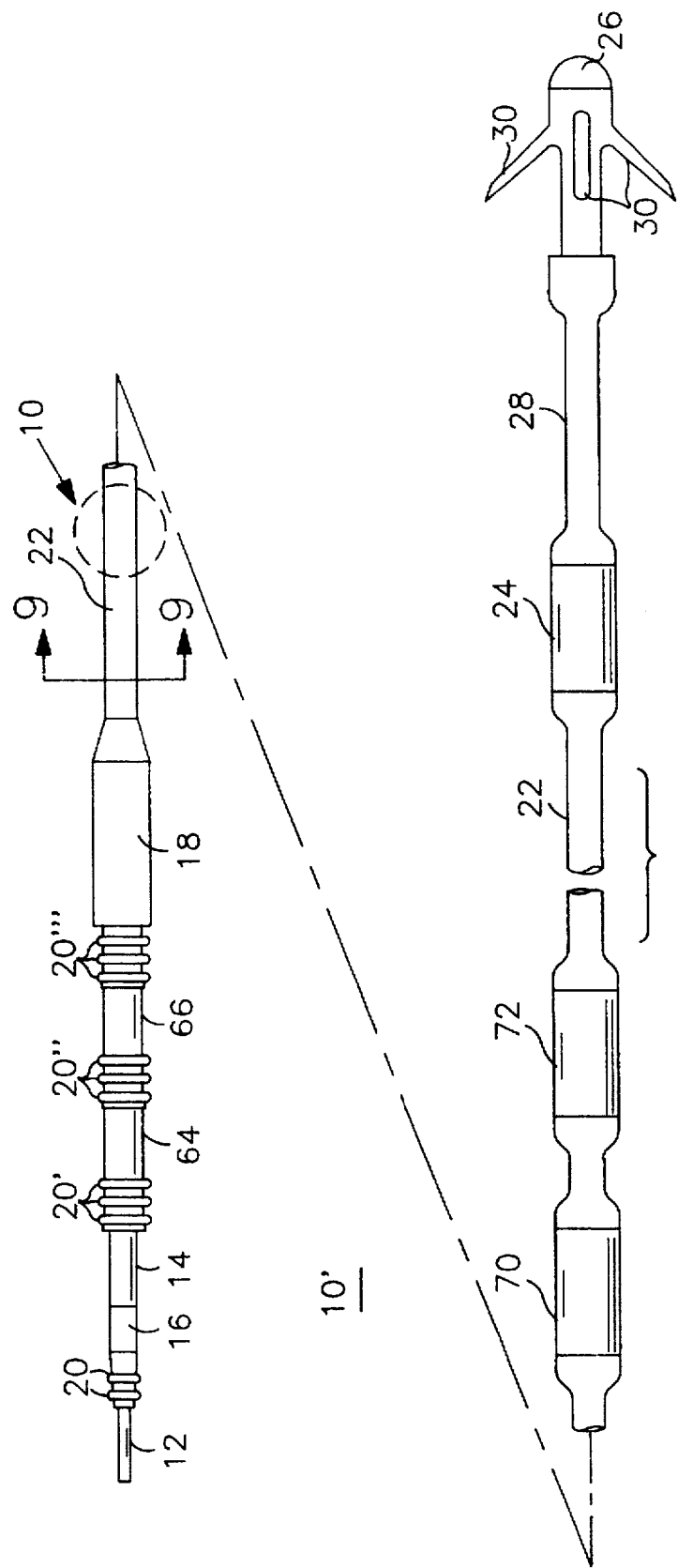
FIG. 8 is a schematic illustration of an exemplary cardiac lead having coaxially arranged, parallel-wound coiled conductor wires in accordance with a further embodiment of the present invention.

For example, FIG. 8 is a schematic illustration of an exemplary atrial and ventricular cardiac pacing lead 10' in which the present invention may be implemented. In this embodiment, a pair of proximal atrial ring electrodes 70 and 72 are adapted to be placed in the right atrium for sensing atrial depolarizations, and the distal tip electrode 26 and distal ring electrode 24 are adapted to be placed in the right atrial apex for pacing the ventricle and sensing ventricular depolarizations. The connector elements 12, 14, 64 and 66 are adapted to be coupled with a VDD type pacemaker pulse generator that provides the known atrial synchronous, ventricular inhibited pacing mode. In this coaxial arrangement, a set of outer coiled wire conductors are parallel-wound to share a common outer winding diameter and to surround a set of inner coiled wire conductors that are similarly parallel-wound to share a common inner winding diameter. The coiled wire conductors may take any of the forms described herein.

Figure 9:
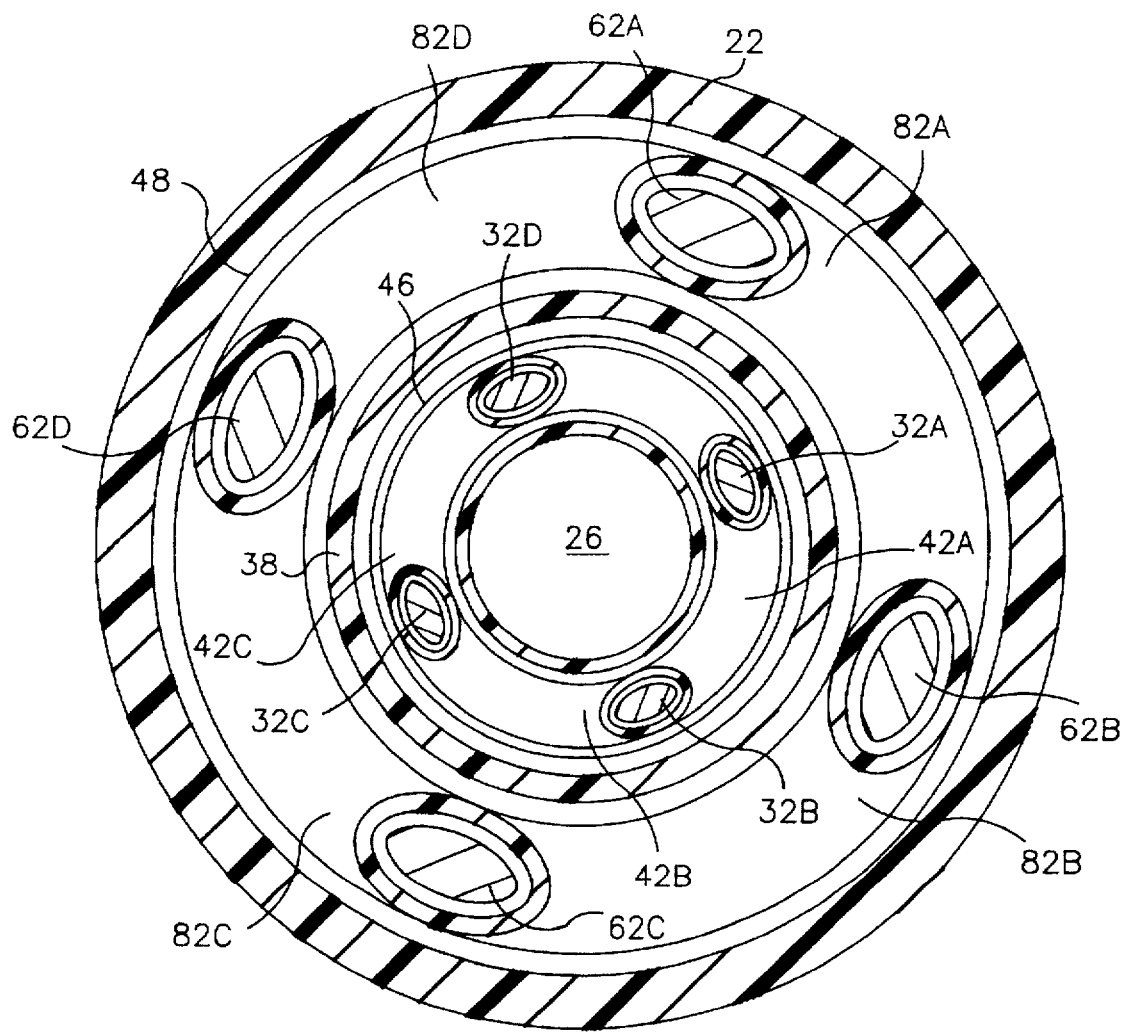
FIG. 9 is an end cross-section view of the lead body taken along lines 9—9 in FIG. 8 showing first and second parallel-wound, individually insulated coiled wire conductor sets arranged coaxially about a central lumen.

FIG. 9 is an end cross-section view of the lead 10' taken along lines 9—9 in FIG. 8 showing inner and outer parallel-wound, individually insulated coiled wire conductor sets 32A–32D and 62A–62D arranged coaxially about a central lumen 26. In this case, first and second pairs of the inner coiled wire conductors 32A, 32B and 32C, 32D are electrically coupled together and form lead conductors extending from the proximal end of the lead body to the distal end thereof and to a distal ring electrode 24 and distal tip electrode 26 in the manner described above with reference to FIG. 1.

Similarly, the outer parallel-wound coiled wire conductors 62A, 62B and 62C, 62D are electrically coupled together and form lead conductors extending from the ring connector elements 64 and 66 at the proximal end of the lead body to the pair of proximal ring electrodes 70 and 72 shown in FIG. 9. Again, each of the coiled wire conductors 62A, 62B, 62C, 62D are received loosely within the lumens of the respective coiled insulative sheaths 82A, 82B, 82C, 82D. A further separating sheath 38 is provided intermediate the inner insulative sheath 27 and the outer insulative sheath 22, whereby inner and outer ring-shaped lumens 46 and 48 are formed for receiving the inner and outer sets of coiled insulative sheaths 42A–42D and 82A–82D.

Although, the wire and sheath diameters of the inner set of coiled wire conductors 32A–32D and insulative sheaths 42A–42D are depicted to be smaller than the wire and sheath diameters of the outer set of coiled wire conductors 62A–62D and insulative sheaths 82A–82D, it will be understood that they may be the same in practice.

Figure 10:
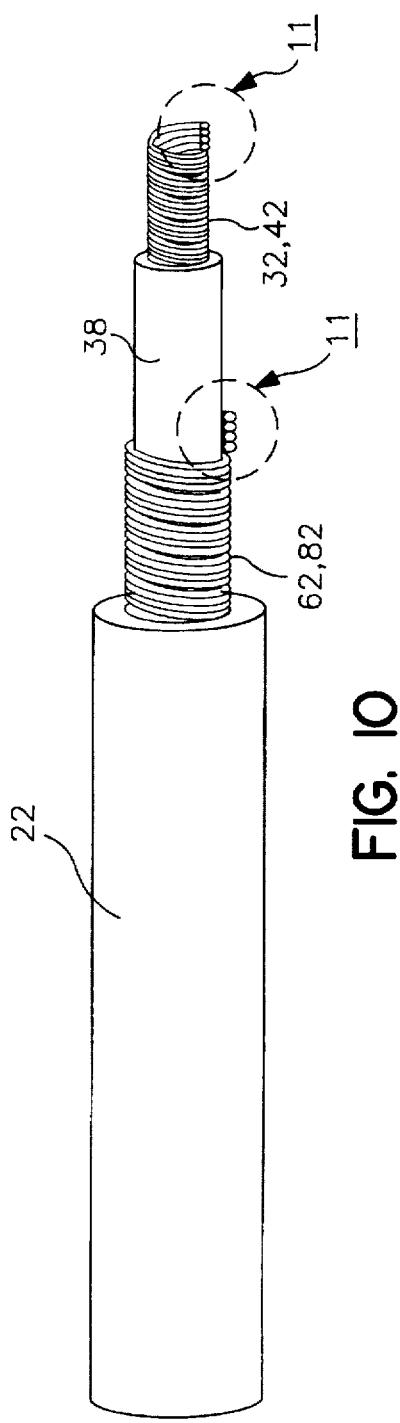
FIG. 10 is an isometric view of section 10 of the lead body depicted in FIG. 8 depicting the internal coaxial arrangement of first and second sets of parallel-wound coiled wire conductors.
Figure 11:
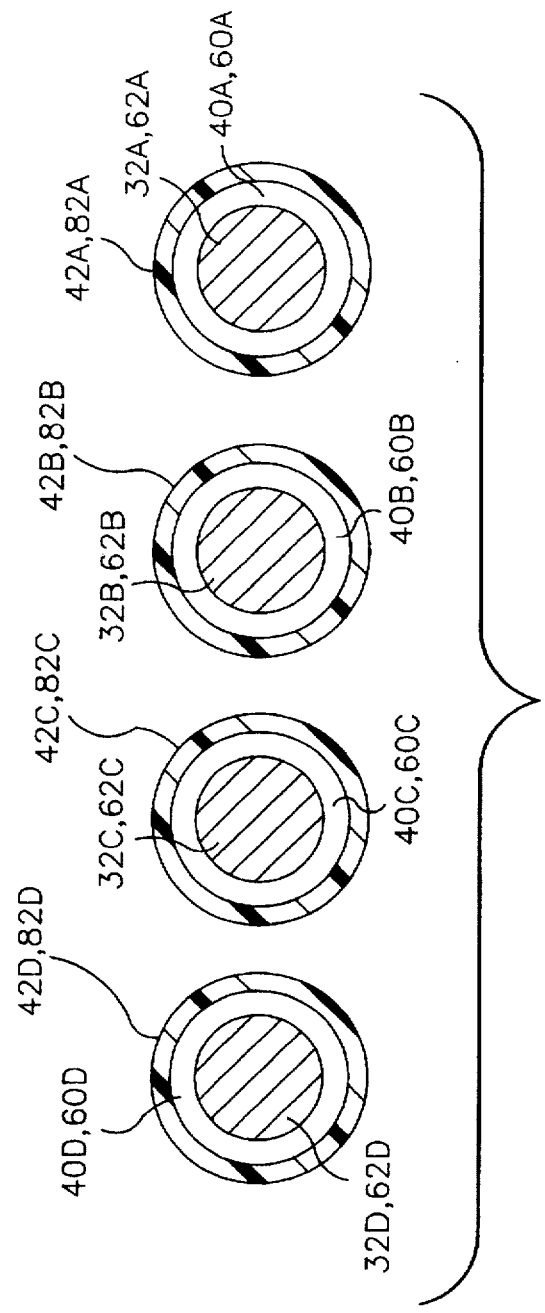
FIG. 11 is an end cross-section view taken at sections 11 and 11' in FIG. 10 showing the end views of the sets of parallel wound coiled wire conductors received within the lumens of respective coiled insulative sheaths.

FIG. 10 is an isometric view of section 10 of the lead body depicted in FIG. 8 depicting the internal coaxial arrangement of first and second sets of parallel-wound coiled wire conductors. FIG. 11 is an end cross-section view taken at sections 11 and 11' in FIG. 10 showing the end views of the sets of parallel wound coiled wire to conductors received within the lumens of respective coiled insulative sheaths. The outer coiled wire conductors may be paired redundantly with the atrial ring electrodes 70 and 72.

Alternatively, the proximal ring electrodes 70 and 72 may be replaced by four ring electrodes or four, orthogonally arranged ring segment electrodes arranged along the lead body so that the four electrodes reside in the atrium when the distal tip electrode 26 and distal ring electrode 24 are placed in the right ventricle. In this case, the outer coiled wire conductors 62A, 62B, 62C, 62D may be individually connected to the respective atrial electrodes.

Figure 12:
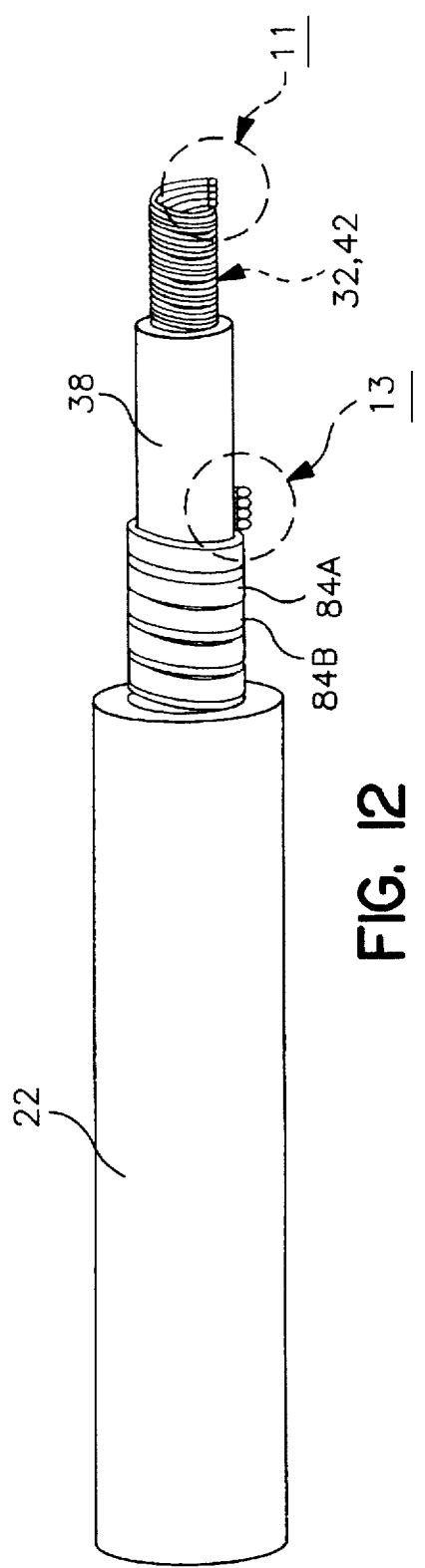
FIG. 12 is an isometric view of section 10 of the lead body depicted in FIG. 8 depicting the internal coaxial arrangement of first and second sets of parallel-wound coiled wire conductors in an alternative arrangement of parallel-wound, redundant coiled wire lead conductors received within the lumen of a single coiled insulative sheath having an elongated cross-section profile that may be substituted for separately insulated coiled wire conductors that are electrically connected in common in any of the above embodiments.
Figure 13:
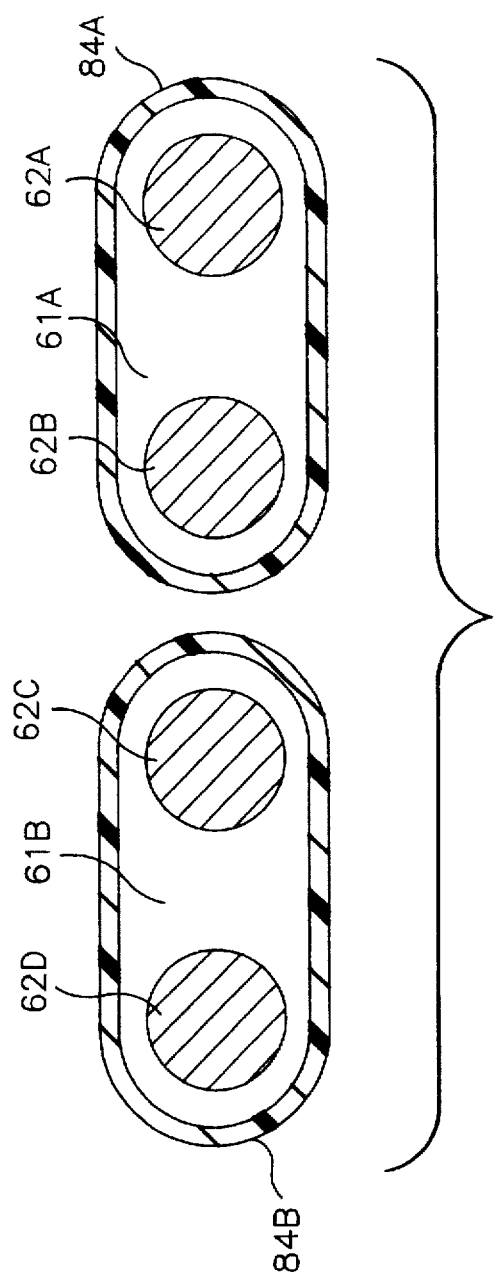
FIG. 13 is an end cross-section view taken at section 13 in FIG. 12 showing the end views of the sets of parallel wound coiled wire conductors received within the lumens of respective elongated cross-section, coiled insulative sheaths.

FIG. 12 is an isometric view of section 10 of the lead body depicted in FIG. 8 depicting the internal coaxial arrangement of first and second sets of parallel-wound, coiled wire conductors in an alternative arrangement. FIG. 13 is an end cross-section view taken at section 13 in FIG. 12 showing the end views of the sets of parallel-wound, coiled wire conductors received within the lumens of respective elongated cross-section, coiled insulative sheaths. Two pairs of parallel-wound, redundant coiled wire lead conductors 62A, 62B and 62C, 62D are received within the lumens 61A and 61B, respectively, of coiled insulative sheaths 84A and 84B, respectively.

As shown in FIGS. 10 and 12, the number of inner coiled wire conductors 32 and coiled insulative sleeves 42 may differ from the number of outer coiled wire conductors 62 and coiled insulative sheaths 82.

The present invention may also be implemented in a coaxial winding configuration with or without an inner separating sheath 38. In the simplest bipolar variation, all of the outer coiled wire conductors 62A–62D may be electrically connected in common as one polarity and all of the inner coiled wire conductors 32A–32D may be electrically connected together as the other polarity. By extension, it will be understood that the number of coiled wire conductors and coiled insulative sheaths of each polarity may differ from the depicted number, and may be reduced in the simplest variation to a single coiled wire conductor and coiled insulative sheath in each case.

In each of the above-described embodiments, it is assumed that all of the coiled wire conductors are insulated by a coiled insulative sheath that loosely receives it. It is contemplated that in certain medical lead designs in accordance with the teachings of the present invention, not all of the parallel-wound (or coaxial) single or redundantly connected coiled wire conductors need to be so insulated. For example, returning to the lead of FIG. 1, assume a lead body formed with two coiled wire conductor pairs effected by redundantly connecting conductor 32A with conductor 32B between proximal pin 12 and distal tip electrode 26 and conductor 32C with conductor 32D between proximal ring connector element 14 and distal ring electrode 24. The invention contemplates not employing coiled insulative sheaths enclosing one of the pairs of conductors and relying on the coiled insulative sheaths receiving the coiled wire conductors of the other pair. Of course, this variation may be incorporated in any of the embodiments of the invention.

Furthermore, in the embodiments described and depicted above of lead conductor bodies and biomedical leads, the pluralities of coiled wire conductors loosely received in respective coiled wire sheaths are parallel-wound and/or coaxially wound within the outer insulative sheath with respect to the outer insulative sheath axis, generally providing an inner lumen for receiving a stiffening stylet. It will be understood that the invention contemplates side-by-side bundling of such coiled wire conductors within coiled insulative sheaths all extending within the lumen of the outer insulative sheath off center from the axis thereof and not necessarily providing for a central stylet receiving lumen or any stylet receiving lumen. In this manner, the biomedical lead conductor body may be further miniaturized. Such biomedical leads not having the stylet receiving lumen may be introduced through an introducer sheath or other structure known in the art.

Turning to the fabrication of the coiled wire conductors and the coiled insulative sheaths as described above, it will be appreciated that the insulative sheath may be formed about the respective conductor wire or cable in an extrusion process that provides for the gap or space 40. Alternatively, the conductor wire(s) or cable(s) may be threaded into a tubular insulative sheath lumen. Then, depending on the configuration of the lead body, each conductor wire(s) or cable(s) and respective insulative sheath may be coiled into a coil shape so that the enclosed coiled wire conductor and coiled insulative sheath share a common pitch. Leads of the types described above may be fabricated in a manner known in the art.

The coiled insulative sheaths 42, 82, 84 may be formed of a wide variety of biocompatible, biostable, non-conductive polymer materials including the aforementioned PTFE and ETFE, as well as other fluoropolymers, e.g., tetrafluoroethylene-hexafluoropropylene-vinylidene fluoride (THV), fluorinated ethylene propylene (FEP), polyfluoroalkoxyl (PFA), polychlorotrifluoroethylene (PCTFE), polyvinylidene fluoride (PVDF), and high durometer polyurethanes, e.g., Pellethane 75D and Tecothane 75D, etc. Any of the known types of conductive wires used in biomedical leads including the above-referenced single filar wires, multi-filar cables, e.g. 1×7, 7×7 cables or the like, single composition or composites or coated wires may be employed is the practice of the invention and in each of the above-described embodiments thereof. The invention may be practiced employing wire cross-section and corresponding coiled insulative sheath cross-section shapes differing form the depicted circular shapes, e.g. elliptical or rectangular shapes.

While the present invention has primary utility in implantable cardiac lead conductors for use in conducting pacing pulse or cardioversion/defibrillation shock energy or for conducting cardiac electrical signals, it will be understood that it may be used in any type of biomedical stimulation or sensing lead to provide high reliability and strength in withstanding stresses encountered in use.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

We claim:

1. A biomedical lead conductor body of the type comprising:

a first coiled wire conductor formed of a first electrical wire having a predetermined wire diameter and wound into a first coil extending between proximal and distal first wire ends; and a first insulative sheath formed in a coil and having a first coiled insulative sheath lumen having a diameter exceeding the predetermined wire diameter of said first coiled wire conductor, loosely receiving said first coiled wire conductor therein, for electrically insulating coil turns of said first coiled wire conductor whereby any corrosion occurring from a defect in the first insulative sheath may extend over a portion of a wire surface beyond a first portion of the wire surface adjacent to the defect.

2. The biomedical lead conductor body of claim 1 further comprising:

a second coiled wire conductor formed of a second electrical wire having a predetermined wire diameter and wound into a second coil extending between proximal and distal second wire ends.

3. The biomedical lead conductor body of claim 2 further comprising:

a second insulative sheath formed in a coil and having a second insulative sheath lumen having a diameter exceeding the predetermined wire diameter of said second coiled wire conductor loosely receiving said second coiled wire conductor therein for electrically insulating adjacent coil turns of said second coiled wire conductor and for avoiding concentrated damage to the second coiled wire conductor within and adjacent to a defect in the second insulative sheath.

4. The biomedical lead conductor body of claim 3 wherein said first and second coiled wire conductors and insulative sheaths are parallel-wound with one another in an intertwined relation about a substantially common winding diameter.

5. The biomedical lead conductor body of claim 3 wherein said first and second coiled wire conductors and insulative sheaths are wound in differing first and second winding diameters with respect to a common winding axis.

6. The biomedical lead conductor body of claim 1 further comprising:

an elongated outer sheath of bio-compatible electrically insulative material extending between proximal and distal outer sheath end regions and enclosing said coiled insulative sheath within an outer sheath lumen.

7. A biomedical lead conductor body of the type comprising:

an elongated outer sheath of bio-compatible electrically insulative material extending between proximal and distal outer sheath ends and enclosing an outer sheath lumen;

first and second coiled wire conductors each formed of electrical wire having a predetermined wire diameter and space wound into a coil, said first and second coiled wire conductors wound with one another about a substantially common axis extending within said outer sheath lumen for pre-determined first and second respective distances between said proximal and distal outer sheath ends; and a first coiled insulative sheath formed in a coil and having a first coiled insulative sheath lumen having a diameter exceeding the predetermined wire diameter of said first coiled wire conductor, loosely receiving said first coiled wire conductor therein, for electrically insulating said first coiled wire conductor from said second coiled wire conductor and for avoiding concentrated damage to the first coiled wire conductor within and adjacent to a defect in said first coiled insulative sheath.

8. The biomedical lead conductor body of claim 7 further comprising:

a second coiled insulative sheath formed in a coil and having a second coiled insulative sheath lumen having a diameter exceeding the predetermined wire diameter of said second coiled wire conductor, loosely receiving said second coiled wire conductor therein, for electrically insulating said first coiled wire conductor and said second coiled wire conductor and for avoiding concentrated damage to the coiled wire conductor within and adjacent to a defect in the insulative sheath enclosing it.

9. The biomedical lead conductor body of claim 8 wherein said first and second coiled wire conductors and insulative sheaths are parallel-wound with one another in an intertwined relation about a substantially common winding diameter.

10. The biomedical lead conductor body of claim 8 wherein said first and second coiled wire conductors and insulative sheaths are wound in differing first and second winding diameters with respect to a common winding axis.

11. A biomedical lead comprising:

a first wire conductor formed of a first electrical wire having a predetermined wire diameter and wound into a first coil extending between proximal and distal first wire ends;

a second coiled wire conductor formed of a second electrical wire having a predetermined wire diameter and wound into a second coil extending between proximal and distal second wire ends;

a first insulative coiled sheath formed in a coil and having a first insulative sheath lumen having a diameter exceeding the predetermined wire diameter of said first coiled wire conductor, loosely receiving said first coiled wire conductor therein;

a second insulative coiled sheath formed in a coil and having a second insulative sheath lumen having a diameter exceeding the predetermined wire diameter of said second coiled wire conductor, loosely receiving said second coiled wire conductor therein;

said first and second coiled insulative sheaths electrically insulating adjacent coil turns of said first coiled wire conductor and said second coiled wire conductor for minimizing concentrated damage to the first and second coiled wire conductors within and adjacent to any defects in the first and second insulative sheaths;

an elongated outer sheath of bio-compatible electrically insulative material extending between proximal and distal outer sheath end regions and enclosing said first and second coiled insulative sheaths within an outer sheath lumen;

a first electrical connector element positioned along said proximal outer sheath end region and coupled to said proximal first wire end;

a second electrical connector element positioned along said proximal outer sheath end region and coupled to said proximal second wire end;

a first operative element formed in said distal outer sheath end region and coupled to said distal first wire end; and a second operative element formed in said distal outer sheath end region and coupled to said distal second wire end.

12. The biomedical lead of claim 11 wherein said first and second coiled wire conductors and insulative sheaths are parallel-wound with one another in an intertwined relation about a substantially common winding diameter.

13. The biomedical lead of claim 11 wherein said first and second coiled wire conductors and insulative sheaths are wound in differing first and second winding diameters with respect to a common winding axis.

14. The biomedical lead of claim 1 wherein at least one of said first and second coiled wire conductors are formed of a multi-filar cable formed of a plurality of wire filars.

15. A biomedical lead body comprising:

N coiled wire conductors each formed of electrical wire having a predetermined wire diameter and space wound into a coils extending between proximal and distal wire ends;

N coiled insulative sheaths, each coiled insulative sheath formed in a coil and having an insulative sheath lumen having a diameter exceeding the predetermined wire diameter of a respective one of said N coiled wire conductors, loosely receiving one of said N coiled wire conductors therein, said N insulative sheaths electrically insulating adjacent coil turns of said N coiled wire conductors and minimizing concentrated damage to the coiled wire conductors within and adjacent to a defect in any of said insulative sheaths; and an elongated outer sheath of bio-compatible electrically insulative material extending between proximal and distal outer sheath end regions and enclosing said N coiled insulative sheaths within an outer sheath lumen.

16. The biomedical lead conductor body of claim 15 wherein said N coiled wire conductors and insulative sheaths are parallel-wound with one another in an intertwined relation about a substantially common winding diameter.

17. The biomedical lead conductor body of claim 15 wherein said N coiled wire conductors and insulative sheaths are wound in differing first and second winding diameters with respect to a common winding axis.

18. The biomedical lead conductor body of claim 15 wherein at least certain ones of said N coiled wire conductors are electrically connected in common at their proximal and distal wire ends.

19. A biomedical lead conductor body comprising:

a plurality $N_1$ of first coiled wire conductors each formed of a first electrical wire having a predetermined wire diameter and wound into respective first coils extending between proximal and distal first wire ends, a like plurality $N_1$ of first insulative coiled sheaths each formed in a coil and having a first insulative sheath lumen having a diameter exceeding the predetermined wire diameter of said plurality of first coiled wire conductors loosely receiving a respective first coiled wire conductor therein;

said plurality $N_1$ of first coiled wire conductors and first coiled insulative sheaths parallel-wound with one another in an intertwined relation about a substantially common winding diameter;

a plurality $N_2$ of second coiled wire conductors each formed of a second electrical wire having a predetermined wire diameter and wound into a respective second coils extending between proximal and distal second wire ends;

a like plurality $N_2$ of second insulative coiled sheaths each formed in a coil and having a second insulative sheath lumen having a diameter exceeding the predetermined wire diameter of said plurality of second coiled wire conductors loosely receiving a respective second coiled wire conductor therein;

said plurality $N_2$ of second coiled wire conductors and second coiled insulative sheaths parallel-wound with one another in an intertwined relation about a substantially common winding diameter;

said first and second coiled insulative sheaths electrically insulating adjacent coil turns of said first coiled wire conductor and said second coiled wire conductor for minimizing concentrated damage to the first and second coiled wire conductors within and adjacent to any defects in the first and second insulative sheath; and an elongated outer sheath of bio-compatible electrically insulative material extending between proximal and distal outer sheath end regions and enclosing said first and second coiled insulative sheaths within an outer sheath lumen.

20. The biomedical lead conductor body of claim 19 wherein said pluralities $N_1$ and $N_2$ of coiled wire conductors and insulative sheaths are parallel-wound with one another in an intertwined relation about a substantially common winding diameter.

21. The biomedical lead conductor body of claim 20 wherein:

said plurality $N_1$ of coiled wire conductors are electrically connected in common at their proximal and distal first wire ends.

22. The biomedical lead conductor body of claim 20 wherein:

said plurality $N_2$ of coiled wire conductors sheaths are electrically connected in common at their proximal and distal second wire ends.

23. The biomedical lead conductor body of claim 19 wherein:

said plurality $N_1$ of coiled wire conductors and insulative sheaths are wound in a first winding diameter with respect to the axis of said outer insulative sheath defining a first coil lumen; and said plurality $N_2$ of coiled wire conductors and insulative sheaths are wound in a second winding diameter with respect to the axis of said outer insulative sheath within said first coil lumen.

24. The biomedical lead conductor body of claim 23 wherein:

said plurality $N_1$ of coiled wire conductors are electrically connected in common at their proximal and distal first wire ends.

25. The biomedical lead conductor body of claim 23 wherein:

said plurality $N_2$ of coiled wire conductors sheaths are electrically connected in common at their proximal and distal second wire ends.

26. The biomedical lead conductor body of claim 19 formed into a biomedical lead wherein:

said first plurality $N_1$ of coiled wire conductors are electrically connected in common at their proximal and distal first wire ends; and said plurality $N_2$ of coiled wire conductors sheaths are electrically connected in common at their proximal and distal second wire ends;

said biomedical lead further comprising:
- a first electrical connector element positioned along said proximal outer sheath end region and coupled to said proximal first wire ends;
- a second electrical connector element positioned along to said proximal outer sheath end region and coupled to said proximal second wire ends;
- a first operative element formed in said distal outer sheath end region and coupled to said distal first wire ends; and
- a second operative element formed in said distal outer sheath end region and coupled to said distal second wire ends.

27. The biomedical lead conductor body of claim 19 formed into a biomedical lead further comprising:
- a plurality $N_1$ of first electrical connector elements positioned along said proximal outer sheath end region and coupled to said proximal first wire ends;
- a plurality $N_2$ of second electrical connector elements positioned along to said proximal outer sheath end region and coupled to said proximal second wire ends;
- a plurality $N_1$ of first operative element formed in said distal outer sheath end region and coupled to said distal first wire ends; and
- a plurality $N_2$ of second operative element formed in said distal outer sheath end region and coupled to said distal second wire ends.

28. A lead conductor body according to claim 1 wherein said first coiled wire is a stranded wire.

29. A lead conductor body according to claim 28 wherein said first coiled wire is a cable.

30. A lead according to claim 11 wherein said first coiled wire is a stranded wire.

31. A lead according to claim 30 wherein said first coiled wire is a cable.

* * * * *